US008283286B2

(12) United States Patent
Saito

(10) Patent No.: US 8,283,286 B2
(45) Date of Patent: Oct. 9, 2012

(54) THERMOSENSITIVE RECORDING MATERIAL

(75) Inventor: Hajime Saito, Sabae (JP)

(73) Assignee: Nicca Chemical Co., Ltd., Fukui-Shi, Fukui (JP)

( * ) Notice: Subject to any disclaimer, the term of this patent is extended or adjusted under 35 U.S.C. 154(b) by 458 days.

(21) Appl. No.: 12/733,152

(22) PCT Filed: Aug. 22, 2008

(86) PCT No.: PCT/JP2008/065481

§ 371 (c)(1),
(2), (4) Date: Feb. 11, 2010

(87) PCT Pub. No.: WO2009/025400

PCT Pub. Date: Feb. 26, 2009

(65) Prior Publication Data

US 2010/0152043 A1 Jun. 17, 2010

(30) Foreign Application Priority Data

Aug. 23, 2007 (JP) ................................ 2007-216882
Jul. 14, 2008 (JP) ................................ 2008-182664

(51) Int. Cl.
*B41M 5/333* (2006.01)
*C07C 37/14* (2006.01)

(52) U.S. Cl. .............. 503/216; 568/31; 568/32; 568/33; 568/34

(58) Field of Classification Search ........................ None
See application file for complete search history.

(56) References Cited

U.S. PATENT DOCUMENTS

| | | | |
|---|---|---|---|
| 3,539,375 | A | 11/1970 | Baum et al. |
| 6,037,308 | A | 3/2000 | Sato et al. |

FOREIGN PATENT DOCUMENTS

| | | | |
|---|---|---|---|
| JP | 43-04160 | | 2/1968 |
| JP | 45-14039 | | 5/1970 |
| JP | 07-149713 | A | 6/1995 |
| JP | 10-029969 | A | 2/1998 |
| JP | 2000-135868 | A | 5/2000 |
| JP | 2001-232949 | A | 8/2001 |
| JP | 2008-280283 | A | 11/2008 |

*Primary Examiner* — Bruce H Hess
(74) *Attorney, Agent, or Firm* — Holtz Holtz Goodman & Chick PC

(57) ABSTRACT

A thermosensitive recording material which comprises a color forming layer comprising a color forming substance, which comprises a colorless or light color leuco dye, and a color developer and disposed on a support, wherein a mixture of (A) at least one compound selected from 4-hydroxy-4'-allyloxydiphenylsulfone, 4-hydroxy-4'-ethyloxydiphenylsulfone and 4-hydroxy-4'-n-propoxydiphenylsulfone and (B) a diphenylsulfone bridged compound represented by general formula (1):

(1)

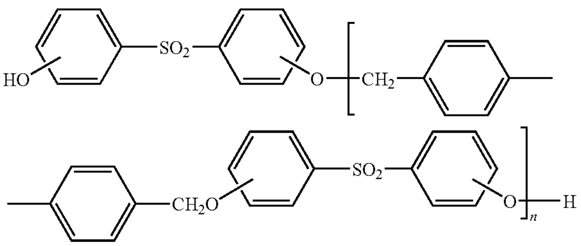

n representing an integer of 1 to 10, in amounts such that the ratio of the amounts by mass of (A) to (B) is 85:15 to 25:75 is used as the color developer. In the thermosensitive recording material, color is formed with a great density, image portions exhibit excellent properties for storage, in particular, excellent resistance to plasticizers, and portions of no color formation exhibit excellent properties for storage, in particular, excellent heat resistance.

1 Claim, No Drawings

THERMOSENSITIVE RECORDING MATERIAL

This application is the United States national phase application of International Application PCT/JP2008/065481 filed Aug. 22, 2008.

TECHNICAL FIELD

The present invention relates to a thermosensitive recording material and, more particularly, to a thermosensitive recording material which exhibits a great sensitivity and provides image portions and portions of no color formation exhibiting excellent properties for storage.

BACKGROUND ART

A thermosensitive recording material is, in general, a material in which a thermosensitive color forming layer containing an electron donating colorless or light color dye precursor and an electron accepting color developing substance as the main components is formed on a support. When the thermosensitive recording material is heated by a heated head, a heated pen or laser beams, the dye precursor and the color developing substance react instantaneously, and a recorded material can be obtained. Development of the thermosensitive recording material has been conducted for a long time. For example, as the thermosensitive sheet for copying obtained by a specific coating treatment on the surface and comprising a composition which is colorless in the conventional form and develops color by heating or irradiation with infrared light, a thermosensitive sheet for copying in which the component developing color by reaction comprises a dye base of the lactone type, the lactam type or the sultone type having no color, an organic acid and a substance melting by heating, is proposed (Patent Reference 1). As the thermosensitive recording material which exhibits improved moisture resistance and stability in printing and can prevent coloring during drying of record-forming components in a formed coating layer and preparation of the record due to the improved moisture resistance, a thermosensitive recording material in which the record-forming unit comprises a support of a sheet material comprising a crystal violet lactone and a phenolic substance, the phenolic substance is a substance which is solid at the room temperature and, at the temperature of the thermograph, is liquefied or vaporized and reacts with the lactone to form a record, and the lactone and the phenolic substance are dispersed in polyvinyl alcohol, is proposed (Patent Reference 2).

Since the thermosensitive recording materials exhibit advantages in that records can be obtained using a relatively simple apparatus, maintenance is easy, and little noise is generated, the thermosensitive recording materials are used for thermal printers for various types of portable terminals, printers for medical images attached to ultrasonic echo apparatuses, thermopen recorders in cardiographs and analytical instruments, tickets for airplanes and trains and POS labels for merchandises.

Various properties such as excellent property for color formation, color formation with a great density using a small amount of heat, excellent properties for storage of obtained images and excellent property for maintaining whiteness in portions of no color formation are required for the thermosensitive recording materials. In particular, reliability on recorded images is important for labels for foods processed by microwave ovens, parking tickets, labels for delivery and various tickets, and excellent properties for storage such as oil resistance, moisture resistance and heat resistance are required. To satisfy the requirement, various compounds have been examined as the color developer for the thermosensitive recording material.

For example, thermosensitive recording materials comprising α,α'-bis[4-(p-hydroxyphenylsulfonyl)phenoxy]-p-xylene, α,α'-bis[4-(p-hydroxyphenylsulfonyl)phenoxy]-m-xylene or α,α'-bis[4-(p-hydroxyphenylsulfonyl)phenoxy]-o-xylene as the color developer providing a thermo-sensitive recording material which exhibits a great sensitivity, suppresses undesirable coloring of the background and exhibits excellent properties for storage which are, in particular, water resistance and resistance to plasticizers, are proposed (Patent Reference 3). As the color developer exhibiting excellent properties for storage of developed images which are, in particular, excellent resistance to plasticizers, oil resistance, light resistance and moisture resistance under heating, diphenylsulfone bridged compounds which are reaction products of dihydroxydiphenylsulfone and an alkylene dichloride or α,α'-dichloro-xylene are shown as examples (Patent Reference 4). However, the thermosensitive recording materials described above exhibit insufficient heat resistance in portions of no color formation, and the requirement for excellent storage of the color developer is not sufficiently satisfied, either.

[Patent Reference 1] Japanese Patent Application Publication No. Showa 43 (1968)-4160

[Patent Reference 2] Japanese Patent Application Publication No. Showa 45 (1970)-14039

[Patent Reference 3] Japanese Patent Application Laid-Open No. Heisei 7 (1995)-149713

[Patent Reference 4] Japanese Patent Application Laid-Open No. Heisei 10 (1998)-29969

DISCLOSURE OF THE INVENTION

Problems to be Overcome by the Invention

Under the above circumstances, the present invention has an object of providing a thermosensitive recording material in which color is formed with a great density, image portions exhibit excellent properties for storage, in particular, excellent resistance to plasticizers, and portions of no color formation exhibit excellent properties for storage, in particular, excellent heat resistance.

Means for Overcoming the Problems

As the result of intensive studies by the present inventors to achieve the above object, it was found that a thermosensitive recording material in which color was formed with a great density, image portions exhibited excellent properties for storage, and portions of no color formation exhibited excellent properties for storage could be obtained by using a mixture of a specific dihydroxydiphenylsulfone monoether-based compound and a diphenylsulfone bridged compound as the color developer. The present invention has been completed based on the knowledge.

The present invention provides:

(1) A thermosensitive recording material which comprises a color forming layer comprising a color forming substance, which comprises a colorless or light color leuco dye, and a color developer and disposed on a support, wherein a mixture of (A) at least one compound selected from 4-hydroxy-4'-allyloxydiphenylsulfone, 4-hydroxy-4'-ethyloxydiphenylsulfone and 4-hydroxy-4'-n-propoxydiphenylsulfone and (B) a diphenylsulfone bridged compound represented by general formula (1):

(1)

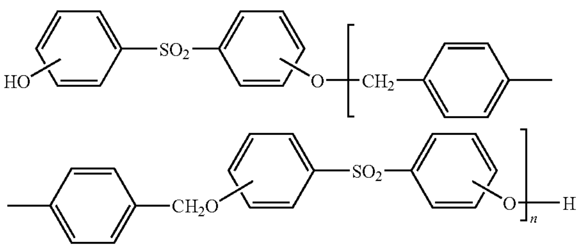

n representing an integer of 1 to 10, in amounts such that a ratio of amounts by mass of (A) to (B) is 85:15 to 25:75 is used as the color developer.

The Effect of the Invention

In accordance with the present invention, a thermosensitive recording material in which color is formed with a great density, image portions exhibit excellent properties for storage, in particular, excellent resistance to plasticizers, and portions of no color formation exhibit excellent properties for storage, in particular, excellent heat resistance can be provided by using a mixture of a specific dihydroxydiphenylsulfone monoether-based compound and a diphenylsulfone bridged compound as the color developer.

THE MOST PREFERRED EMBODIMENT TO CARRY OUT THE INVENTION

The thermosensitive recording material of the present invention is characterized in that, in the thermosensitive recording material which comprises a color forming layer comprising a color forming substance, which comprises a colorless or light color leuco dye, and a color developer and disposed on a support, a mixture of (A) at least one compound selected from 4-hydroxy-4'-allyloxydiphenylsulfone, 4-hydroxy-4'-ethyloxydiphenylsulfone and 4-hydroxy-4'-n-propoxydiphenylsulfone and (B) a diphenylsulfone bridged compound represented by general formula (1) in amounts such that a ratio of the amounts by mass of (A) to (B) is 85:15 to 25:75 is used as the color developer.

(Color Developer)

In the present invention, the properties for storage of image portions can be remarkably improved by using, as the color developer, (A) the 4,4'-dihydroxydiphenylsulfone monoether-based compound which is at least one compound selected from 4-hydroxy-4'-allyloxydiphenylsulfone, 4-hydroxy-4'-ethyloxydiphenylsulfone and 4-hydroxy-4'-n-propoxydiphenylsulfone and (B) the specific diphenylsulfone bridged compound represented by general formula (1) in combination in comparison with the properties for storage of image portions exhibited by using the 4,4'-dihydroxydiphenylsulfone monoether-based compound of component (A) alone. The density of the formed color in the image portion can be remarkably improved in comparison with that obtained by using component (B), which is the diphenylsulfone bridged compound represented by general formula (1), alone.

The ratio of the amount by mass of the 4,4'-dihydroxydiphenylsulfone monoether-based compound of component (A) to the amount by mass of the diphenylsulfone bridged compound represented by general formula (1) of component (B) is in the range of 85:15 to 25:75. When the relative amount of the diphenylsulfone bridged compound represented by general formula (1) of component (B) is less than the above range, there is the possibility that the properties for storage of image portions becomes poor. When the relative amount of the 4,4'-dihydroxydiphenylsulfone monoether-based compound of component (A) is less than the above range, there is the possibility that the density of color formation in image portions is decreased. It is preferable that the ratio of the amount of component (A) to the amount of component (B) is 80:20 to 30:70 and more preferably 70:30 to 40:60.

[Production of (A) the 4,4'-dihydroxydiphenylsulfone monoether-based Compound]

As an example of the 4,4'-dihydroxydiphenylsulfone monoether-based compound of component (A), 4-allyloxy-4'-hydroxydiphenylsulfone can be produced by the reaction of 4,4'-dihydroxydiphenylsulfone and an allyl halide in the presence of a base and, where necessary, using a solvent. It is preferable that the temperature of the reaction is in the range of 20° C. or higher and the temperature of refluxing of the solvent or lower. Examples of the allyl halide used in the above include allyl chloride and allyl bromide. Examples of the base used in the above include sodium hydroxide, potassium hydroxide, triethylamine and pyridine. Examples of the solvent used in the above include water, methanol, ethanol, propanol, isopropanol and mixtures of these solvents. 4-Allyloxy-4'-hydroxydiphenylsulfone produced above occasionally contains byproducts of preparation such as 4,4'-diallyloxydiphenylsulfone, 3-allyl-4,4'-dihydroxydiphenylsulfone, 3-allyl-4-allyloxy-4'-hydroxy-diphenylsulfone and 3-allyl-4-hydroxy-4'-allyloxydiphenylsulfone 4-Hydroxy-4'-ethyloxydiphenylsulfone and 4-hydroxy-4'-n-propoxy-diphenylsulfone can be produced in accordance with similar procedures.

[Production of (B) the Diphenylsulfone Bridged Compound]

The diphenylsulfone bridged compound represented by general formula (1) which is used as component (B) can be produced, for example, by the reaction of dihydroxydiphenylsulfone and 4,4'-bis-(chloromethyl)-1,1'-biphenyl or 4,4'-bis(bromomethyl)-1,1'-biphenyl in the presence of a basic substance using a solvent. It is preferable that the temperature of the reaction is in the range of 50° C. or higher and the temperature of refluxing of the solvent or lower. Examples of the dihydroxydiphenylsulfone used in the above include 4,4'-dihydroxy-diphenylsulfone, 2,4'-dihydroxydiphenylsulfone and mixtures of these compounds. Examples of the basic substance used in the above include sodium hydroxide, potassium hydroxide, sodium carbonate, potassium carbonate, triethylamine and pyridine. Examples of the solvent used in the above include alcohols such as methanol, ethanol, propanol, isopropanol, butanol and isobutanol; glycols such as ethylene glycol, propylene glycol, diethylene glycol and dipropylene glycol; monoalkyl ethers of glycols; dialkyl ethers of glycols; ketones such as acetone; nitriles such as acetonitrile; ethers such as tetrahydrofuran; esters such as methyl acetate, dimethyl carbonate and propylene carbonate; amides such as N-methylformamide and N,N-dimethylformamide; sulfoxides such as dimethyl sulfoxide; and mixtures of these solvents.

(Color Forming Substance)

In the present invention, the colorless or light color leuco dye used as the color forming substance comprised in the thermosensitive color forming layer is not particularly limited. Examples of the leuco dye include fluorane derivatives, quinazoline derivatives, phthalide derivatives, triphenylmethane derivatives and phenothiazine derivatives. Among these leuco dyes, fluorane derivatives are preferable due to the excellent color forming property. Examples of the fluorane derivative, which is a leuco dye, include 3-diethylamino-6-methyl-7-anilinofluorane, 3-diethylamino-6-methyl-7-(2',4'-dimethylanilino)fluorane, 3-diethylamino-6-methyl-7-chlorofluorane, 3-dibutylamino-6-methyl-7-anilinofluorane, 3-diamylamino-6-methyl-7-anilinofluorane, 3-(N-methyl-N-propyl)amino-6-methyl-7-anilinofluorane, 3-(N-methyl-N-butyl)amino-6-methyl-7-anilinofluorane, 3-(N-methyl-N-amyl)amino-6-methyl-7-anilinofluorane, 3-(N-methyl-N-cyclohexyl)amino-6-methyl-7-anilinofluorane, 3-(N-ethyl-N-propyl)amino-6-methyl-7-anilinofluorane, 3-(N-ethyl-N-amyl)amino-6-methyl-7-anilinofluorane, 3-(N-ethyl-N-isoamyl)amino-6-methyl-7-anilinofluorane, 3-[N-ethyl-N-(4-methylphenynl)]amino-6-methyl-7-anilinofluorane, 3-(N-ethyl-N-cyclohexyl)amino-6-methyl-7-anilinofluorane, 3-(N-pentyl-N-cyclohexyl)amino-6-methyl-7-anilinofluorane, 3-(N-hexyl-N-isoamyl)amino-6-methyl-7-anilinofluorane, 3-diethyl-N-butylamino-7-(2'-fluoroanilino) fluorane, 3-(N-methyl-N-cyclohexyl)amino-6-chlorofluorane, 3-pyrrolidyl-7-dibenzylaminofluorane, 3-bis (diphenyl-amino)fluorane, 3-diethylamino-6-chloro-7-anilinofluorane, 3-diethyl-amino-7-(2'-chloroanilino) fluorane, 3-dibutylamino-7-(2'-chloroanilino)-fluorane, 3-diethylamino-7-chlorofluorane, 3-butylamino-7-(2'-chloroanilino)fluorane, 3-diethylamino-6-ethoxyethyl-7-anilinofluorane and 3-diethylamino-7-dibenzylaminofluorane.

The leuco dye described above may be used singly or in combination of two or more. The amount of the color forming substance comprised in the thermosensitive color forming layer can be suitably selected in accordance with the characteristics of the thermosensitive recording material to be obtained.

(Sensitizer)

In the thermosensitive recording material of the present invention, the thermosensitive color forming layer may further comprise a sensitizer. The sensitizer used in the above is not particularly limited. Examples of the sensitizer include amides of fatty acids such as stearamide and palmiamide, 1,2-diphenoxyethane, 1,2-bis(4-methylphenoxy)ethane, 1,2-bis(3-methylphenoxy)ethane, 1,2-bis(phenoxymethyl)benzene, 1,3-bis-(phenoxymethyl)benzene, 1,4-bis(phenoxymethyl)benzene, 1,2-bis(3-methylphenoxymethyl)benzene, 1,3-bis(3-methylphenoxymethyl)benzene, 1,4-bis(3-methylphenoxymethyl)benzene, 1,2-bis(4-methylphenoxymethyl)benzene, 1,3-bis(4-methylphenoxymethyl)benzene, 1,4-bis(4-methylphenoxymethyl)benzene, 2-benzyloxynaphthalene, dibenzyl oxalate, di(4-methylbenzyl)oxalate, di(4-chlorobenzyl)oxalate, 4-acetylbenzil, N-phenyltoluenesulfonamide, naphthyl toluenesulfonate, p-benzyl-biphenyl, m-terphenyl, 4,4'-dipropoxydiphenylsulfone, 4,4'-diisopropoxydiphenylsulfone, 4,4'-diallyloxydiphenylsulfone, 2,4'-dipropoxydiphenylsulfone, 2,4'-diisopropoxydiphenylsulfone, 2,4'-diallyloxydiphenylsulfone, benzyl p-benzyloxybenzoate and benzyl terephthalate. The sensitizer described above may be used singly or in combination of two or more.

(Image Stabilizer)

In the thermosensitive recording material of the present invention, the thermosensitive color forming layer may further comprise an image stabilizer. The image stabilizer used in the above is not particularly limited. Examples of the image stabilizer include 4-benzyloxy-4'-(2-methylglycidyloxy) diphenylsulfone, 4,4'-diglycidyloxydiphenylsulfone, 4,4'-butylidenebis(3-methyl-6-t-butylphenol), 2,2'-di-t-butyl-5,5'-dimethyl-4,4'-sulfonylphenol, 1,1,3-tris(2-methyl-4-hydroxy-5-t-butylphenyl)butane, 1,1,3-tris(2-methyl-4-hydroxy-5-cyclohexylphenyl)butane, compounds having the polyester structure such as polyhydroxybenzoic acids, substances having the urethane structure such as urea urethanes and substances having the polyether structure such as poly (phenylsulfone)ethers. The image stabilizer may be used singly or in combination of two or more.

(Filler and Other Additives)

In the thermosensitive recording material of the present invention, the thermosensitive color forming layer may comprise a filler, where necessary. Examples of the filler used in the above include inorganic fillers such as silica, calcium carbonate, kaolin, baked kaolin, diatomaceous earth, clay, talc, titanium oxide, aluminum hydroxide, zinc oxide, zinc hydroxide, barium sulfate and silica treated on the surface; and organic fillers such as polystyrene microballs, nylon powder, urea-formaline resin fillers, particles of silicone resins, cellulose powder, particles of styrene/methacrylic acid copolymers, particles of vinylidene chloride-based resins, particles of styrene/acrylic monomer copolymers and spherical hollow fine particles of plastics. The filler may be used singly or in combination of two or more.

In the thermosensitive recording material of the present invention, the thermosensitive color forming layer may comprise other additives, where necessary. Examples of the additive include lubricants such as stearic acid ester wax, polyethylene wax and zinc stearate; benzophenone-based ultraviolet light absorbers such as 2-hydroxy-4-benzyloxybenzophenone; triazole-based ultraviolet light absorbers such as benzotriazole and 2-(2'-hydroxy-5'-methylphenyl)benzotriazole; agents for providing water resistance such as glyoxal; dispersants; defoaming agents; antioxidants and fluorescent dyes.

[Production of the Thermosensitive Recording Material]

The process for producing the thermosensitive recording material of the present invention is not particularly limited. The thermosensitive recording material of the present invention can be produced by preparing a coating fluid for a thermosensitive color forming layer by dispersing the color forming substance, the color developer and components which are used where necessary such as the sensitizer, the image stabilizer and other components in combination with a suitable binder in a suitable medium such as an aqueous medium, followed by coating a support with the coating fluid prepared above and drying the formed coating film. It is preferable that the dispersion comprising the color forming substance, the color developer and the sensitizer is prepared by separately preparing a dispersion comprising the color forming substance, a dispersion comprising the color developer and a dispersion comprising the sensitizer, followed by mixing the prepared dispersions.

It is preferable that the color forming substance, the color developer and the sensitizer are dispersed in the form of fine particles in each dispersion. Therefore, it is preferable that a sand mill or a ball mill is used for preparing the dispersions.

(Binder)

The binder used in the above is not particularly limited. Examples of the binder include cellulose derivatives such as hydroxyethylcellulose, methylcellulose, methoxycellulose, ethylcellulose and carboxymethyl-cellulose, polyvinyl alcohols such as polyvinyl alcohol, polyvinyl alcohol modified with carboxyl group, polyvinyl alcohol modified with sulfonic group, polyvinyl alcohol modified with silicones and polyvinyl alcohol modified with amides, natural macromolecules such as gelatin, casein, starch and alginic acid, polyacrylic acid, polyacrylic acid esters, polyvinyl acetate, polymethacrylic acid esters, vinyl chloride/vinyl acetate copolymers, ethylene/vinyl acetate copolymers, vinyl acetate/acrylic acid ester copolymers, polyacrylamide; acrylamide/acrylic acid ester copolymers, acrylamide/acrylic acid ester/methacrylic acid terpolymers, isobutylene/maleic anhydride copolymers, styrene/acrylic acid ester copolymers, styrene/butadiene copolymers, styrene/butadiene/acrylic monomer copolymers, styrene/maleic anhydride copolymers, methyl vinyl ether/maleic anhydride copolymers; polyethylene modified with carboxyl group, polyvinyl alcohol/acrylamide block copolymers, polyvinyl-pyrrolidone, melamine-formaldehyde resins, urea-formaldehyde resins, polyurethanes, polyamide resins, petroleum resins and terpene resins. The binder may be used singly or in combination of two or more.

(Support, Undercoating Layer and Backcoating Layer)

The support used in the thermosensitive recording material of the present invention is not particularly limited. Examples of the support include paper such as neutral paper and acidic paper, synthetic paper, regenerated paper using pulp of used paper, films, nonwoven fabrics and woven fabrics.

In the present invention, it is preferable that an undercoating layer and a backcoating layer comprising an inorganic filler or an organic filler is disposed on the support. Examples of the inorganic filler include silica, calcium carbonate, kaolin, baked kaolin, diatomaceous earth, clay, talc, titanium oxide, aluminum hydroxide, zinc oxide, zinc hydroxide, barium sulfate and silica treated on the surface. Examples of the organic filler include polystyrene microballs, nylon powder, urea-formaline resin fillers, particles of silicone resins, cellulose powder, particles of styrene/methacrylic acid copolymers, particles of vinylidene chloride-based resins, particles of styrene/acrylic monomer copolymers and spherical hollow fine particles of plastics, When the undercoating layer and the backcoating layer are formed, these layers work as thermal insulating layers, and sensitivity is increased by effectively utilizing the thermal energy from a thermal head and the like. In particular, an undercoating layer and a backcoating layer comprising spherical hollow fine particles of plastics are preferable since the thermal sensitivity can be effectively increased.

The spherical hollow fine particles are fine hollow particles which have been expanded to have a structure such that the particles have a shell of a thermoplastic resin and contain the air or other gases at the inside, and the average diameter of the particles is about 0.2 to 20 μm. When the average diameter (the outer diameter of the particle) is smaller than 0.2 μm, a drawback arises with respect to the cost due to the problem in production such as the difficulty in achieving the desired porosity. When the average diameter exceeds 20 μm, the thermosensitive recording material is brought into contact with the thermal head less tightly due to decrease in the smoothness of the surface after the coating film is dried, and the effect of increasing the thermal sensitivity is decreased. Therefore, it is preferable that the particles have an average diameter within the above range, and the distribution of the diameter is narrow. It is preferable that the porosity of the spherical hollow particles of plastics is 40% or greater and more preferably 90% or greater from the standpoint of the thermal insulation. When the porosity is small, thermal energy from the thermal head is discharged to the outside of the thermosensitive recording material via the support due to the insufficient effect of thermal insulation, and the effect of increasing the thermal sensitivity is poor. The "porosity" described above means the ratio of the inner diameter to the outer diameter of a hollow fine particle, which is expressed by the following equation:

$$\text{porosity (\%)}=[(\text{inner diameter of hollow fine particle})/(\text{outer diameter of hollow fine particle})]\times 100$$

As described above, the spherical hollow fine particle of plastics has a shell of a thermoplastic resin. Examples of the thermoplastic resin include polystyrene, polyvinyl chloride, polyvinylidene chloride, polyvinyl acetate, polyacrylic acid ester, polyacrylonitrile, polybutadiene and copolymer resins derived from these resins. Among these thermoplastic resins, copolymer resins comprising vinylidene chloride and acrylonitrile as the main components are preferable.

The binder used for the undercoating layer and the backcoating layer is not particularly limited. Examples of the binder include cellulose derivatives such as hydroxyethylcellulose, methylcellulose, methoxy-cellulose, ethylcellulose and carboxymethylcellulose, polyvinyl alcohols such as polyvinyl alcohol, polyvinyl alcohol modified with carboxyl group, polyvinyl alcohol modified with sulfonic group, polyvinyl alcohol modified with silicones and polyvinyl alcohol modified with amides, natural macromolecules such as gelatin, casein, starch and alginic acid, polyacrylic acid, polyacrylic acid esters, polyvinyl acetate, polymethacrylic acid esters, vinyl chloride/vinyl acetate copolymers, ethylene/vinyl acetate copolymers, vinyl acetate/acrylic acid ester copolymers, polyacrylamide, acrylamide/acrylic acid ester copolymers, acrylamide/acrylic acid ester/methacrylic acid terpolymers, isobutylene/maleic anhydride copolymers, styrene/acrylic acid ester copolymers, styrene/butadiene copolymers, styrene/butadiene/acrylic monomer copolymers, styrene/maleic anhydride copolymers, methyl vinyl ether/maleic anhydride copolymers, polyethylene modified with carboxyl group, polyvinyl alcohol/acrylamide block copolymers, polyvinylpyrrolidone, melamine-formaldehyde resins, urea-formaldehyde resins; polyurethanes, polyamide resins, petroleum resins and terpene resins.

In the thermosensitive recording material of the present invention, where necessary, an overcoat layer may be formed on the thermosensitive color forming layer using a resin soluble in water such as cellulose derivatives and polyvinyl alcohol, an emulsion soluble in water of styrene-butadiene copolymers and terpene resins, a resin insoluble in water or a composition obtained by adding fillers, monomers and oligomers such as isocyanates and unsaturated compounds and crosslinking agents to these resins.

The thermosensitive recording material of the present invention may be a multicolor thermosensitive recording material in which a plurality of layers are formed by using color forming substances forming different color tones for each thermosensitive color forming layer.

EXAMPLES

The present invention will be described more specifically with reference to examples in the following. However, the present invention is not limited to the examples.

The propertips of thermosensitive recording materials prepared in Examples and Comparative Examples were evaluated in accordance with the following methods.

(1) Resistance to plasticizers

Color formation was conducted on a prepared thermosensitive recording material using a thermosensitive printing apparatus [product of OHKURA ELECTRIC Co., Ltd.] under a printing voltage of 20 V and a pulse width of 3 ms, and the color density at a portion where color was formed (an image portion) was measured using a reflection densitometer [product of MACBETH Co., Ltd; "Model RD-918"]. Then, three sheets of a wrapping film of polyvinyl chloride were placed on the image portion in a manner such that one sheet was placed on top of another, and ten sheets of conventional paper were placed on the sheets of polyvinyl chloride in the same manner. A weight was placed on the resultant composite sheet so that a pressure of about 1.96 N/$cm^2$ was applied. After the composite sheet was left standing for 24 hours under the environment of 20° C., the color density was measured.

(2) Moisture Resistance

Color formation was conducted on a prepared thermosensitive recording material using a thermosensitive printing apparatus [product of OHKURA ELECTRIC Co., Ltd.] under a printing voltage of 20 V and a pulse width of 3 ms, and the color density at a portion where color was formed (an image portion) was measured using a reflection densitometer [product of MACBETH Co., Ltd; "Model RD918"]. After the material was left standing for 24 hours under the environment of 60° C. and 80% RH, the color density of the image portion was measured.

(3) Heat Resistance

The color density of a prepared thermosensitive recording material at a portion where color was not formed (a portion of no color formation) was measured using a reflection densitometer [product of MACBETH Co., Ltd; "RD-918"]. After the material was left standing for 24 hours at 80° C. or 90° C., the color density of the portion of no color formation was measured.

Synthesis Example 1

Into a four-necked flask equipped with a stirrer, a reflux condenser and a thermometer, 35 g (0.14 moles) of 4,4'-dihydroxydiphenylsulfone (the purity: 99.8% by mass), 15 g (0.06 moles) of 2,4'-dihydroxydiphenylsulfone (the purity: 96.5% by mass) and 200 g of dimethylformamide were placed, and a solution was prepared. To the prepared solution, 14 g (0.35 moles) of sodium hydroxide was added, and the resultant mixture was heated at 70° C. Then, a solution obtained by dissolving 38 g (0.15 moles) of 4,4'-bis(chloromethyl)-1,1'-biphenyl into 120 g of dimethylformamide was added dropwise over 0.5 hours. After the addition was completed, the resultant mixture was heated at 110° C., and the reaction was allowed to proceed for 5 hours. After the reaction was completed, the reaction product was slowly added into 2,000 g of a 0.1% by mass aqueous solution of hydrochloric acid at 30° C. over 0.5 hours, and the resultant mixture was stirred for 2 hours. The formed crystals were separated by filtration and washed with water. The obtained crystals and 500 g of a 20% by mass aqueous solution of methanol were placed into a reactor. The reaction mixture was heated at 70° C. for 2 hours and, then, cooled at 25° C. The formed crystals were separated by filtration, washed with water and dried, and 70 g of a reaction product was obtained. The obtained reaction product was analyzed in accordance with the gel permeation chromatography [product of TOSO Corporation] (the moving phase being dimethylformamide (DMF)) and was found to be a mixture of compounds represented by general formula (1) in which n represents an integer of 1 to 9 as shown in the following:

n=0: the retention time: 12.9 minutes; the area (%): 4.9
n=1: the retention time: 12.0 minutes; the area (%): 23.2
n=2: the retention time: 11.2 minutes; the area (%): 23.7
n=3: the retention time: 10.7 minutes; the area (%): 19.1
n=4: the retention time: 10.4 minutes; the area (%): 12.7
n=5: the retention time: 10.0 minutes; the area (%): 7.3
n=6: the retention time: 9.7 minutes; the area (%): 3.3
n=7: the retention time: 9.4 minutes; the area (%): 1.2
n=8: the retention time: 9.2 minutes; the area (%): 0.3
n=9: the retention time: 8.9 minutes; the area (%): 0.1

Synthesis Example 2

In accordance with the same procedures as those conducted in Synthesis Example 1 except that sodium hydroxide was used in an amount of 9.2 g (0.23 moles) in place of 14 g (0.35 moles), and 4,4'-bis(chloromethyl)-1,1'-biphenyl was used in an amount of 25.3 g (0.1 mole) in place of 38 g (0.15 moles), 52 g of a reaction product was obtained. The composition of the obtained product was as follows:

n=0: 8.9%; n=1: 39.8%; n=2: 26.8%; n=3: 12.1%; n=4: 5.0%; n=5: 2.1%; n=6: 0.5%; n=7: 0.3%; n=8: 0.2% ("%" meaning "% by area")

Synthesis Example 3

In accordance with the same procedures as those conducted in Synthesis Example 1 except that 4,4'-dihydroxydiphenylsulfone (the purity: 99.8% by mass) was used in an amount of 50 g (0.2 moles) in place of 35 g (0.14 moles), and 2,4'-dihydroxydiphenylsulfone was not used, 69 g of a reaction product was obtained. The composition of the obtained product was as follows:

n=0: 4.7%; n=1: 24.1%; n=2: 23.1%; n=3: 18.8%; n=4: 12.5%; n=5: 7.2%; n=6: 3.5%; n=7: 1.5%; n=8: 0.4%; n=9: 0.2% ("%" meaning "% by area")

Example 1

A dispersion of a color forming substance (Fluid A) was prepared by dispersing 10 parts by mass of 3-dibutylamino-6-methyl-7-anillinofluorane and 10 parts by mass of a 10% by mass aqueous solution of polyvinyl alcohol into 30 parts by mass of water by micropulverization for 4 hours using a sand mill. A dispersion of a color developer (Fluid B) was prepared by dispersing 3 parts by mass of the compound obtained in Synthesis Example 1, 7 parts by mass of 4-hydroxy-4'-allyloxydiphenylsulfone and 10 parts by mass of a 10% by mass aqueous solution of polyvinyl alcohol into 30 parts by mass of water by micropulverization for 3 hours using a sand mill. A dispersion of silica gel (Fluid C) was prepared by dispersing 10 parts by mass of silica [product of MIZUSAWA INDUSTRIAL CHEMICALS, Ltd.; "MIZUKASIL (a registered trade name) P527" and 10 parts by mass of a 10% by mass aqueous solution of polyvinyl alcohol into 30 parts by mass of water by micropulverization for 3 hours using a sand mill. A dispersion of zinc stearate (Fluid D) was prepared by dispersing 10 parts by mass of zinc stearate and 10 parts by mass of a 10% by mass aqueous solution of polyvinyl alcohol into 30 parts by mass of water by micropulverization for 3 hours using a sand mill. A resin fluid (Fluid E) was prepared by mixing 40 parts by mass of nonexpandable plastic fine hollow particles (the content of solid components: 24% by mass; the average diameter of particles: 3 μm; the porosity: 90%) and 10 parts by mass of a latex of a styrene/butadiene copolymer [product of ZEON Corporation; "NIPOL (a registered trade name) LX438C] with 50 parts by mass of water under stirring using a disper. A coating fluid for a color forming layer was prepared by mixing 5 parts by mass of Fluid A, 20 parts by mass of Fluid B, 20 parts by mass of Fluid C and 2.5 parts by mass of Fluid D under stirring using a disper. A coating fluid for an undercoating layer was prepared by mixing 5 parts by mass of Fluid C and 10 parts by mass of Fluid E under stirring using a disper. The prepared coating fluid for an undercoating layer was applied to a high quality paper having a unit weight of 60 g/$m^2$ in an amount such that the amount of the coating material after being dried was 3 $g/m^2$. The formed coating layer was dried, and a paper having an undercoating layer was obtained. The coating fluid for a color forming layer prepared above was applied to the undercoating layer of the paper obtained above in an amount such that the amount of the coating material after being dried was 5 $g/m^2$, and the formed coating layer was dried. After the obtained paper was treated by calendering under a pressure of 1 MPa, a thermosensitive recording material of the present invention was obtained, and the obtained material was evaluated. The results of the evaluation are shown in Table 1.

Example 2

A thermosensitive recording material was prepared and evaluated in accordance with the same procedures as those conducted in Example 1 except that the dispersion of a color developer (Fluid B) was prepared using 4-hydroxy-4'-ethyloxydiphenylsulfone in place of 4-hydroxy-4'-allyloxydiphenylsulfone. The results of the evaluation are shown in Table 1.

Example 3

A thermosensitive recording material was prepared and evaluated in accordance with the same procedures as those conducted in Example 1 except that the dispersion of a color developer (Fluid B) was prepared using 4-hydroxy-4'-n-propoxydiphenylsulfone in place of 4-hydroxy-4'-allyloxydiphenylsulfone. The results of the evaluation are shown in Table 1.

Example 4

A thermosensitive recording material was prepared and evaluated in accordance with the same procedures as those conducted in Example 1 except that the dispersion of a color developer (Fluid B) was prepared using, in place of 3 parts by mass of the compound obtained in Synthesis Example 1 and 7 parts by mass of 4-hydroxy-4'-allyloxydiphenylsulfone, 5 parts by mass of the compound obtained in Synthesis Example 1 and 5 parts by mass of 4-hydroxy-4'-allyloxydiphenylsulfone, respectively. The results of the evaluation are shown in Table 1.

Example 5

A thermosensitive recording material was prepared and evaluated in accordance with the same procedures as those conducted in Example 1 except that the dispersion of a color developer (Fluid B) was prepared using, in place of 3 parts by mass of the compound obtained in Synthesis Example 1 and 7 parts by mass of 4-hydroxy-4'-allyloxydiphenylsulfone, 4 parts by mass of the compound obtained in Synthesis Example 2 and 6 parts by mass of 4-hydroxy-4'-ethyloxydiphenylsulfone, respectively. The results of the evaluation are shown in Table 1.

Example 6

A thermosensitive recording material was prepared and evaluated in accordance with the same procedures as those conducted in Example 1 except that the dispersion of a color developer (Fluid B) was prepared using, in place of 3 parts by mass of the compound obtained in Synthesis Example 1 and 7 parts by mass of 4-hydroxy-4'-allyloxydiphenylsulfone, 4 parts by mass of the compound obtained in Synthesis Example 3 and 6 parts by mass of 4-hydroxy-4'-n-propoxydiphenylsulfone, respectively. The results of the evaluation are shown in Table 1.

Example 7

A thermosensitive recording material was prepared and evaluated in accordance with the same procedures as those conducted in Example 1 except that the dispersion of a color developer (Fluid B) was prepared using, in place of 3 parts by mass of the compound obtained in Synthesis Example 1 and 7 parts by mass of 4-hydroxy-4'-allyloxydiphenylsulfone, 2 parts by mass of the compound obtained in Synthesis Example 1 and 8 parts by mass of 4-hydroxy-4'-allyloxydiphenylsulfone, respectively. The results of the evaluation are shown in Table 1.

Example 8

A thermosensitive recording material was prepared and evaluated in accordance with the same procedures as those conducted in Example 1 except that the dispersion of a color developer (Fluid B) was prepared using, in place of 3 parts by mass of the compound obtained in Synthesis Example 1 and 7 parts by mass of 4-hydroxy-4'-allyloxydiphenylsulfone, 7 parts by mass of the compound obtained in Synthesis Example 1 and 3 parts by mass of 4-hydroxy-4'-allyloxydiphenylsulfone, respectively. The results of the evaluation are shown in Table 1.

Comparative Example 1

A thermosensitive recording material was prepared and evaluated in accordance with the same procedures as those conducted in Example 1 except that the dispersion of a color developer (Fluid B) was prepared using 10 parts by mass of the compound obtained in Synthesis Example 1 in place of 3 parts by mass of the compound obtained in Synthesis Example 1 and 7 parts by mass of 4-hydroxy-4'-allyloxydiphenylsulfone. The results of the evaluation are shown in Table 1.

Comparative Example 2

A thermosensitive recording material was prepared and evaluated in accordance with the same procedures as those conducted in Example 1 except that the dispersion of a color developer (Fluid B) was prepared using 10 parts by mass of 4-hydroxy-4'-allyloxydiphenylsulfone in place of 3 parts by mass of the compound obtained in Synthesis Example 1 and 7 parts by mass of 4-hydroxy-4'-allyloxydiphenylsulfone. The results of the evaluation are shown in Table 1.

Comparative Example 3

A thermosensitive recording material was prepared and evaluated in accordance with the same procedures as those conducted in Example 1 except that the dispersion of a color developer (Fluid B) was prepared using, in place of 3 parts by mass of the compound obtained in Synthesis Example 1 and 7 parts by mass of 4-hydroxy-4'-allyloxydiphenylsulfone, 1 part by mass of the compound obtained in Synthesis Example 1 and 9 parts by mass of 4-hydroxy-4'-allyloxydiphenylsulfone, respectively. The results are shown in Table 1.

Comparative Example 4

A thermosensitive recording material was prepared and evaluated in accordance with the same procedures as those conducted in Example 1 except that the dispersion of a color developer (Fluid B) was prepared using, in place of 3 parts by mass of the compound obtained in Synthesis Example 1 and 7 parts by mass of 4-hydroxy-4'-allyloxydiphenylsulfone, 9 parts by mass of the compound obtained in Synthesis Example 1 and 1 part by mass of 4-hydroxy-4'-allyloxydiphenylsulfone, respectively. The results of the evaluation are shown in Table 1.

Comparative Example 5

A thermosensitive recording material was prepared and evaluated in accordance with the same procedures as those conducted in Example 1 except that the dispersion of a color developer (Fluid B) was prepared using a condensation product of 4,4'-dihydroxydiphenylsulfone and bis(2-chloroethyl) ether (having phenolic hydroxyl groups at both ends) [product of NIPPON SODA Co., Ltd.; "D-90"] in place of the compound obtained in Synthesis Example 1. The results of the evaluation are shown in Table 1.

Comparative Example 6

A thermosensitive recording material was prepared and evaluated in accordance with the same procedures as those conducted in Example 1 except that the dispersion of a color developer (Fluid B) was prepared using 4-hydroxy-4'-isopropoxydiphenylsulfone [product of NIPPON SODA Co., Ltd.; "D-8"] in place of 4-hydroxy-4'-allyloxydiphenylsulfone. The results of the evaluation are shown in Table 1.

TABLE 1

| | Color density of image portion | | | Color density of portion of no color formation | | |
|---|---|---|---|---|---|---|
| | before test | resistance to plasticizers | moisture resistance | before test | heat resistance at 80° C. | heat resistance at 90° C. |
| Example 1 | 1.23 | 1.14 | 1.23 | 0.09 | 0.09 | 0.15 |
| Example 2 | 1.25 | 1.08 | 1.24 | 0.09 | 0.09 | 0.17 |
| Example 3 | 1.21 | 1.15 | 1.21 | 0.09 | 0.09 | 0.13 |
| Example 4 | 1.19 | 1.07 | 1.18 | 0.09 | 0.09 | 0.17 |
| Example 5 | 1.16 | 1.05 | 1.15 | 0.09 | 0.09 | 0.18 |
| Example 6 | 1.16 | 1.09 | 1.14 | 0.09 | 0.09 | 0.17 |
| Example 7 | 1.23 | 0.95 | 1.15 | 0.09 | 0.11 | 0.19 |
| Example 8 | 1.16 | 1.10 | 1.12 | 0.09 | 0.09 | 0.14 |
| Comparative Example 1 | 0.81 | 0.80 | 0.81 | 0.09 | 0.09 | 0.10 |
| Comparative Example 2 | 1.15 | 0.24 | 0.65 | 0.09 | 0.10 | 0.15 |
| Comparative Example 3 | 1.25 | 0.52 | 0.90 | 0.09 | 0.13 | 0.30 |
| Comparative Example 4 | 0.93 | 0.92 | 0.93 | 0.09 | 0.09 | 0.12 |
| Comparative Example 5 | 1.23 | 1.10 | 1.22 | 0.09 | 0.11 | 0.31 |
| Comparative Example 6 | 1.25 | 0.95 | 1.23 | 0.09 | 0.12 | 0.35 |

As clearly shown in the result in Table 1, the thermosensitive recording materials of the present invention of Examples 1 to 8 in which the diphenylsulfone bridged compound and the dihydroxydiphenylsulfone monoether-based compound, which was one of 4-hydroxy-4'-allyloxydiphenylsulfone, 4-hydroxy-4'-ethyloxydiphenylsulfone and 4-hydroxy-4'-n-propoxydiphenylsulfone, were mixed in a specific ratio of the amounts exhibited more excellent color density, resistance to plasticizers and moisture resistance in image portions and more excellent heat resistance in portions of no color formation in comparison with those exhibited with the thermosensitive recording materials of Comparative Examples 1 to 6.

INDUSTRIAL APPLICABILITY

In the a thermosensitive recording material, color is formed with a great density, image portions exhibit excellent properties for storage, in particular, excellent resistance to plasticizers, and portions of no color formation exhibit excellent properties for storage, in particular, excellent heat resistance.

The invention claimed is:

1. A thermosensitive recording material which comprises a color forming layer comprising a color forming substance, which comprises a colorless or light color leuco dye, and a color developer and disposed on a support, wherein a mixture of (A) at least one compound selected from 4-hydroxy-4'-allyloxydiphenylsulfone, 4-hydroxy-4'-ethyloxydiphenylsulfone and 4-hydroxy-4'-n-propoxydiphenylsulfone and (B) a diphenylsulfone bridged compound represented by general formula (1):

(1)

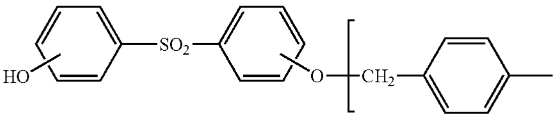

-continued

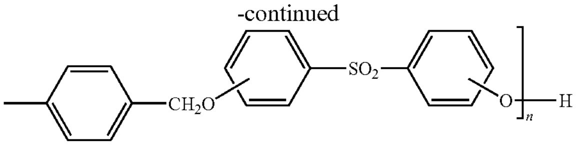

n representing an integer of 1 to 10, in amounts such that a ratio of amounts by mass of (A) to (B) is 85:15 to 25:75 is used as the color developer.

* * * * *